(12) United States Patent
Procino et al.

(10) Patent No.: US 8,318,771 B2
(45) Date of Patent: Nov. 27, 2012

(54) METHOD OF TREATMENT OF NEPHROGENIC DIABETES INSIPIDUS

(75) Inventors: Giuseppe Procino, Bari (IT); Maria Svelto, Bari (IT); Giovanna Valenti, Bari (IT); Monica Carmosino, Bari (IT)

(73) Assignee: Universita' Degli Studi di Bari, Bari (IT)

( * ) Notice: Subject to any disclaimer, the term of this patent is extended or adjusted under 35 U.S.C. 154(b) by 162 days.

(21) Appl. No.: 12/847,553

(22) Filed: Jul. 30, 2010

(65) Prior Publication Data

US 2012/0029001 A1 Feb. 2, 2012

(51) Int. Cl.
*A61K 31/445* (2006.01)
*A61K 31/415* (2006.01)
*A61K 31/40* (2006.01)
*A61K 31/35* (2006.01)

(52) U.S. Cl. ........ 514/316; 514/403; 514/414; 514/422; 514/460; 514/866

(58) Field of Classification Search ................. 514/316, 514/403, 414, 422, 460, 866
See application file for complete search history.

(56) References Cited

OTHER PUBLICATIONS

Procino et al., "Statins: a potential therapeutical tool for treating nephrogenic diabetes insipidus", European Journal of Clinical Investigation, vol. 40, Suppl. 1, pp. 69 (Mar. 2010).*

* cited by examiner

*Primary Examiner* — Kevin E Weddington
(74) *Attorney, Agent, or Firm* — Nixon & Vanderhye P.C.

(57) ABSTRACT

Nephrogenic diabetes insipidus is treated with statins.

9 Claims, 1 Drawing Sheet

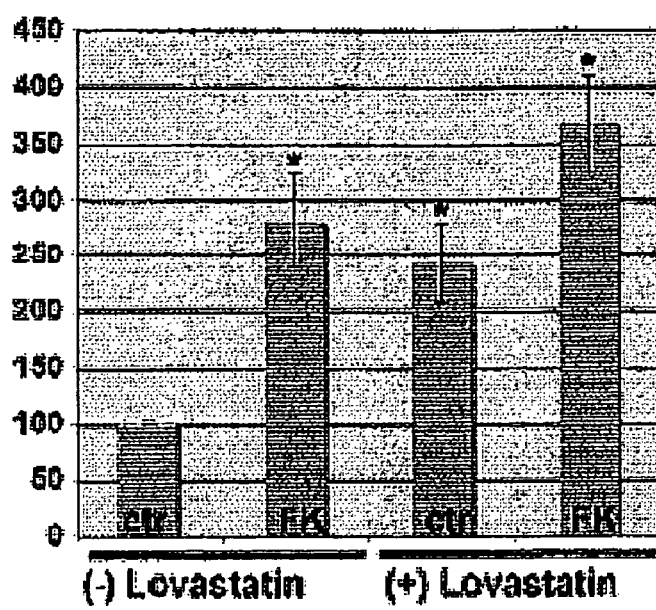
Figure 1 Effect of treatment with lovastatin on the amount of AQP2 expressed on the apical membrane of MCD4 cells in culture

METHOD OF TREATMENT OF NEPHROGENIC DIABETES INSIPIDUS

FIELD OF THE INVENTION

The present invention refers to a new method for treating the consequences of nephrogenic diabetes insipidus (NDI), in particular X-linked type NDI.

TECHNICAL BACKGROUND TO THE INVENTION

In persons suffering from nephrogenic diabetes insipidus (hereinafter NDI), generally X-linked type NDI, the gene for the vasopressin receptor is mutated, hence the mutated protein cannot transduce the signal of the presence of vasopressin in circulation when there is an increase in intracellular cAMP and an increase in aquaporin 2 (AQP2) in the membrane.

In vivo, vasopressin is released by the pituitary gland when the organism needs to limit the amount of water eliminated in the urine. Vasopressin binds its V2R receptor on the main cell of the renal collecting duct, determines a transient cAMP increase in the cells and, consequently, shifts the protein AQP2 from the cell cytoplasm towards the apical membrane which faces into the collecting duct. In these conditions a large amount of water is reabsorbed from the pro-urine and returns into the blood, therefore limiting the amount of water which the organism loses in the urine.

The absence of AQP2 on the membrane prevents the reabsorption of water from the pro-urine causing the production of enormous volumes of urine (up to 50 liters/day), exposing the person affected to the constant danger of dehydration and cardiovascular failure.

At present there is no real cure for NDI, in particular for polyuria which accompanies this pathology. The symptoms are kept under control by guaranteeing patients continuous hydration, administering a low-salt diet and treating them with diuretics based on thiazide, alone or in combination with prostaglandin synthesis inhibitors or potassium saver diuretics in order to reduce the volume of urine produced.

The diuretics hydrochlorothiazide and amyloride, used in NDI, reduce the fraction of sodium reabsorbed in the distal tubule causing hypovolemia. To compensate for this situation, the renin-angiotensin-aldosterone system (RAAS) is activated which, by increasing the blood levels of aldosterone, determines a greater reabsorption of sodium in the proximal tubule. Since the reabsorption of sodium in the proximal tubule is accompanied by an isosmotic transport of water, the overall amount of water reabsorbed in the proximal tubule is increased, consequently reducing the volume of urine arriving at the distal nephron. Unfortunately, however, although the administration of said molecules improves the patient's clinical situation, it has serious side effects. In fact, the thiazide is able to reduce the polyuria but, at the same time, it can deplete the deposits of potassium in the organism. The loss of potassium is in itself a very dangerous condition for the organism and must be kept constantly under control by integration of potassium or amyloride-based treatment.

Another treatment consists in prostaglandin synthesis inhibitors, and in particular indometacin, a non-steroid anti-inflammatory drug which, however, can cause migraine and dizziness, increases the risk of gastrointestinal disorders and, when administered in the first year of life, can increase the risk of kidney disease.

Furthermore, indometacin and thiazide determine a reduction in the glomerular filtration rate (GFR) resulting in an increased risk of nephropathy.

The aspecific inhibitors of cyclooxygenases represent an alternative but this treatment can have significant side effects on cardiac function. Furthermore, in patients undergoing this treatment, the volume of urine is considerably reduced but does not drop below 4-12 liters/day.

SUMMARY OF THE INVENTION

One object of the present invention is to provide a method for treating NDI, and in particular polyuria correlated with NDI, by means of a treatment method which overcomes the drawbacks of the prior art and does not have significant side effects.

It has now been found that statins, widely used in the treatment of hypercholesterolemia, are able to consequently reduce excess loss of urine in patients suffering from NDI.

The object of the invention is therefore achieved by means of a method for treating NDI which comprises administering one or more statins to the patient.

DETAILED DESCRIPTION OF THE INVENTION

According to a first aspect, the invention concerns a method for treating nephrogenic diabetes insipidus (NDI) which comprises administering, to a person requiring it, an effective amount of at least one statin.

In particular, the invention concerns a method for treating polyuria correlated with NDI which comprises administering, to a person requiring it, an effective amount of at least one statin.

According to one embodiment of the invention, said NDI is of the X-linked type.

According to the present invention, "polyuria" indicates the known dysfunction of the urinary system which consists in the emission of an excessive amount of urine, normally more than 2 liters during a 24-hour period. Polyuria accompanies NDI and represents one of the worst consequences of the latter.

According to the invention, "statin" indicates a drug which inhibits the synthesis of endogenous cholesterol, generally acting on the enzyme 3-hydroxy-3-methylglutaryl-CoA reductase. Natural statins and synthetic statins are known. The statins that can be used according to the invention can be chosen from those commercially available, whether they are drugs already active or prodrugs, i.e. biologically inactive molecules which, once administered to the organism, undergo chemical transformations, generally by endogenous enzymes, which make them active molecules.

By way of example, the statin can be selected from the group comprising lovastatin, atorvastatin, fluvastatin, torvastatin, mevastatin, pitavastatin, pravastatin, rosuvastatin and simvastatin.

A preferred statin according to the invention is selected from lovastatin, rosuvastatin and fluvastatin.

More generally the use of hydrosoluble statins which are easily carried via the blood to all the tissues and to the kidney is preferred.

The amounts to be administered vary according to the statin used and, as always, the weight, age, state of health of the patient and seriousness of the pathology.

Normally, the amounts of statin to be administered are equal to the maximum amounts conventionally administered for the treatment of hypercholesterolemia.

By way of example, statins can be used in a range of between 20 and 80 mg/day. For the method of the invention, the statins are administered in the form of pharmaceutical compositions, preferably orally, in the conventional dosage units well known in the art.

The present inventors have therefore found that it is possible to restore normal levels of AQP2 on the luminal membrane of the main renal collecting duct cells by administering statins to the patients. Once expressed on the plasmatic membrane, the AQP2 determines reabsorption of water, correcting the polyuria which affects patients suffering from NDI.

This therapeutic approach is completely new as it aims directly at correcting the defect in the traffic of the AQP2 protein which is at the basis of the pathological phenotype. A further advantage of the therapeutic approach based on the use of statins lies in the absence of severe side effects like those associated with the pharmacological treatment currently used.

In this perspective, statins are able to achieve two fundamental objectives: determine remission of the phenotype with bland transitory side effects, thus representing a considerable technical advance with respect to the current treatments.

The in vitro and in vivo evidence obtained by the present inventors clearly indicates that statins are able to increase the apical levels of AQP2 with an effect comparable to that of vasopressin.

BRIEF DESCRIPTION OF THE FIGURES

FIG. 1 shows the effect of the treatment with lovastatin on the amount of AQP2 expressed on the apical membrane of renal cells in culture.

EXPERIMENTAL SECTION

Example 1

In Vitro Evaluation of the Depletion of Cholesterol on the Accumulation of AQP2 on the Plasmatic Membrane The MCD4 cells, which are in culture and derive from main cells of the renal collecting duct, were treated experimentally with lovastatin. In the cell model, as in the renal tubule in vivo, the presence of AQP2 on the membrane depends on the presence of vasopressin.

In MCD4 cells in the absence of lovastatin in the culture medium (-Lovastatin) and in control (ctr) conditions, the AQP2 is stored in intracellular vesicles. When the levels of cAMP are increased via the use of forskolin (FK) $10^{-5}$ M for 20 min, the AQP2 is shifted by exocytosis to the apical membrane of the same cells. The FK mimes the effect of the vasopressin in in vitro experiments. The same phenomenon occurs in the tubule in vivo following release into the circulation of vasopressin. In the presence of 5 µM lovastatin in the culture medium for 72 h (+Lovastatin) the control (ctr) cells accumulate a considerable amount of AQP2 on the apical membrane. The lovastatin therefore mimes the effect of the FK or the stimulation with vasopressin. If, in addition to the presence of lovastatin, the cells are treated with FK, the increase in the AQP2 on the apical membrane is even more evident. It is possible to quantize the effect of the treatment with lovastatin in terms of accumulation of AQP2 on the apical membrane by means of surface protein biotinylation experiments.

In the absence of lovastatin, only a modest amount of AQP2 is expressed on the apical membrane of the MCD4 cells, and therefore biotinylated, in control cells. This amount is arbitrarily set to 100% in the densitometric analysis shown in FIG. 1. The treatment with FK determines an increase of approximately 3 times in the amount of AQP2 expressed on the apical membrane. Interestingly, treatment of the cells for 72 h with lovastatin alone determines an increase of AQP2 present on the apical membrane comparable to the one obtained by the FK. This result indicates that lovastatin is able to accumulate the AQP2 on the apical membrane even in the absence of intracellular increases of cAMP.

The effect produced by the lovastatin is induced also by other statins such as rosuvastatin and fluvastatin in their hydrosoluble formulation. Also the latter are commonly used in clinical practice for treating hypercholesterolemia.

In vitro tests performed in MCD4 renal cells indicate that the minimum treatment time with statins able to produce an evident shift of the AQP2 in the cells is 6 hours.

Example 2

In Vivo Evaluation of the Effect of Administration of Fluvastatin on the Amount of AQP2 Urine Expressed on the Apical Membrane Adult male mice C56BL6 were treated in acute phase with a dose equal to 10 mg/Kg of body weight of fluvastatin dissolved in sterile physiological solution. The method of administration was intravenous injection via the caudal vein. An identical number of mice were injected with physiological solution only and used as a control. The mice were kept for the following hours with water and food ad libitum. Once 6 hours had elapsed from the infusion, the mice were sacrificed, the kidneys rapidly removed, fixed, embedded and sectioned under cryomicrotome to obtain semi-fine sections of 5 µm on which AQP2 immunolocalization experiments were performed. The interval of 6 hours between the pharmacological treatment and the sacrifice was chosen on the basis of the indications resulting from the in vitro experiments.

With respect to the control condition, in which marking of the AQP2 is localised in intracellular vesicles, in the mice treated with fluvastatin, a significant amount of AQP2 is localised on the apical membrane.

The invention claimed is:

1. A method for the treatment of nephrogenic diabetes insipidus (NDI) which comprises administering, to a subject in need thereof, an effective amount of at least one statin.

2. The method of claim 1, for the treatment of polyuria correlated with NDI.

3. The method of claim 1, wherein said NDI is of the X-linked type.

4. The method of claim 1, wherein said statin is a drug that inhibits the synthesis of endogenous cholesterol.

5. The method of claim 1, wherein said statin is natural or synthetic.

6. The method of claim 1, wherein said statin is chosen from lovastatin, fluvastatin, atorvastatin, mevastatin, pitavastatin, pravastatin, rosuvastatina and simvastatin.

7. The method of claim 1, wherein said statin is chosen from lovastatin, rosuvastatin and fluvastatin.

8. The method of claim 1, wherein said statin is hydrosoluble.

9. The method of claim 1, wherein said statin is administered in effective amounts to inhibit the synthesis of endogenous cholesterol.

* * * * *